United States Patent
Selig

(10) Patent No.: US 9,289,254 B2
(45) Date of Patent: Mar. 22, 2016

(54) ELECTROSURGICAL DEVICE HAVING A TEMPERATURE MEASUREMENT DEVICE, METHOD FOR DETERMINING A TEMPERATURE AND/OR A TEMPERATURE CHANGE AT A NEUTRAL ELECTRODE

(75) Inventor: Peter Selig, Nehren (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1253 days.

(21) Appl. No.: 13/126,846

(22) PCT Filed: Oct. 28, 2009

(86) PCT No.: PCT/EP2009/007722
§ 371 (c)(1),
(2), (4) Date: Apr. 29, 2011

(87) PCT Pub. No.: WO2010/049145
PCT Pub. Date: May 6, 2010

(65) Prior Publication Data
US 2011/0202055 A1  Aug. 18, 2011

(30) Foreign Application Priority Data

Oct. 30, 2008 (DE) .......................... 10 2008 053 841
Mar. 19, 2009 (DE) .......................... 10 2009 013 917

(51) Int. Cl.
| | |
|---|---|
| A61B 18/12 | (2006.01) |
| A61B 5/01 | (2006.01) |
| A61B 5/053 | (2006.01) |
| A61B 18/16 | (2006.01) |
| A61B 18/00 | (2006.01) |

(52) U.S. Cl.
CPC .............. *A61B 18/1206* (2013.01); *A61B 5/01* (2013.01); *A61B 5/053* (2013.01); *A61B 18/1233* (2013.01); *A61B 18/16* (2013.01); *A61B 2018/00702* (2013.01); *A61B 2018/00791* (2013.01); *A61B 2018/00797* (2013.01); *A61B 2018/00875* (2013.01); *A61B 2562/08* (2013.01)

(58) Field of Classification Search
CPC ........... A61B 18/1206; A61B 18/1233; A61B 18/16; A61B 2018/165; A61B 2018/167; A61B 2018/00875; A61B 2018/00755
See application file for complete search history.

(56) References Cited

U.S. PATENT DOCUMENTS

| | | | |
|---|---|---|---|
| 4,416,277 A | 11/1983 | Newton et al. | |
| 6,258,085 B1 * | 7/2001 | Eggleston | ........................ 606/35 |
| 8,231,614 B2 * | 7/2012 | Dunning et al. | ................. 606/32 |
| 2006/0079872 A1 | 4/2006 | Eggleston | |
| 2006/0224150 A1 * | 10/2006 | Arts et al. | ........................ 606/32 |

(Continued)

FOREIGN PATENT DOCUMENTS

| | | |
|---|---|---|
| DE | 35 44 443 A1 | 6/1987 |
| DE | 10 2004 025 613 B4 | 8/2008 |

(Continued)

*Primary Examiner* — Michael Peffley
(74) *Attorney, Agent, or Firm* — Dickstein Shapiro LLP

(57) ABSTRACT

A method for determining a temperature and/or a temperature change at a neutral electrode having a contacting agent layer. The method comprises determining at least one impedance value of the contacting agent layer and calculating a temperature change and/or a temperature at the neutral electrode, at least on the basis of the impedance value. The contacting agent layers may be made from hydrogel and the method uses a correlation that exists between the temperature change and the impedance change.

28 Claims, 2 Drawing Sheets

(56) References Cited

U.S. PATENT DOCUMENTS

| | | | |
|---|---|---|---|
| 2007/0049914 A1* | 3/2007 | Eggleston | 606/32 |
| 2007/0049919 A1 | 3/2007 | Lee, Jr. et al. | |
| 2008/0278179 A1* | 11/2008 | Eisele | 324/682 |
| 2008/0281310 A1* | 11/2008 | Dunning et al. | 606/32 |
| 2012/0109121 A1* | 5/2012 | Gregg | 606/35 |

FOREIGN PATENT DOCUMENTS

| | | |
|---|---|---|
| EP | 1 707 151 A2 | 10/2006 |
| EP | 1 902 684 A1 | 3/2008 |
| EP | 1 990 020 A2 | 11/2008 |

* cited by examiner

US 9,289,254 B2

ELECTROSURGICAL DEVICE HAVING A TEMPERATURE MEASUREMENT DEVICE, METHOD FOR DETERMINING A TEMPERATURE AND/OR A TEMPERATURE CHANGE AT A NEUTRAL ELECTRODE

FIELD OF THE INVENTION

The invention relates to an electrosurgical device having a temperature measurement device and to a method for determining a temperature and/or a temperature change at a neutral electrode.

BACKGROUND

In high frequency (HF) surgery, electrical energy is fed to the tissue to be treated. In this regard, a distinction is generally drawn between monopolar and bipolar application of the high frequency current (HF current).

In a monopolar application, usually only one active electrode is provided, to which the high frequency alternating voltage is applied. The active electrode is situated, for example, at an electrosurgical instrument for cutting and/or coagulating tissue. The application of a neutral electrode to the body of the patient is also required to complete the current circuit through the tissue situated between the active electrode and the neutral electrode. The form of the active electrode depends on the use to which it is put. The surface of the active electrode, by which the alternating current is conducted into the tissue, is relatively small, so that a high current density and consequently a high level of heat generation arise in the direct vicinity of the active electrode.

The current density falls off rapidly with increasing distance away from the active electrode, provided that high current densities do not occur in other body parts as a result of substantial differences in tissue conductivity. The alternating voltage applied to the active electrode is conducted away via the neutral electrode. It should be noted that the neutral electrode is applied over a large area on the body of the patient and presents only a small contact resistance to the high frequency alternating current.

In a bipolar application, two active electrodes are provided, between which the tissue to be treated is accommodated. The flow of current is conducted via the tissue lying between the two active electrodes so that this tissue is heated upon application of an HF current. The majority of the current flows between the two active electrodes.

Sometimes, the neutral electrode is not correctly applied to the patient or the electrode becomes partially detached during treatment. In these cases, the current flow is restricted to the parts of the neutral electrode still making contact, which can lead to a significantly greater impedance at said parts and, in general, to a greater current density within the adjacent tissue. As discussed below with reference to prior art documents, monitoring systems that make an assessment of the application quality of the neutral electrode are known.

For example, DE 10 2004 025 613 B4 discloses a method for determining the contact impedance between two partial electrodes, or electrode sections of a divided neutral electrode, used in high frequency surgery. Herein, the contact impedance is determined between the two electrode sections by an oscillator circuit. It can be assumed that, with the neutral electrode having a large contact area, the contact impedance between the individual sections is significantly lower.

In recent years, treatment methods have been developed whereby relatively large HF currents are applied for a relatively long period. The risk of burning the tissue at the neutral electrode, however, is increased with this method. Thus, even with a correctly applied neutral electrode, damage can still be caused to the tissue depending on the treatment method or the course of the treatment. Theoretically, it is also conceivable to increase the contact area of the neutral electrode, although this is often not practical.

It is therefore necessary to monitor the temperature at the neutral electrode. U.S. application publication no. 2006/0079872 A1 discloses a device for this purpose. According to this publication, a resistor is coupled into the treatment current and the heating of the resistor can be monitored with a heat sensor. The resistor should be selected to substantially simulate the real impedance conditions between the neutral electrode and the active electrode. Suitable selection of the resistor, however, is very difficult because the impedance values change on every application depending on the methods used, the instrument used, the positioning of the instrument and the neutral electrode, the organ being treated, etc.

Other approaches have considered providing commercially available temperature sensors directly on the electrodes. However, the provision of said measurement devices at the electrodes is very complex. In addition, local heating often arise, which may not be detectable by the sensors.

As a rule, the impedance between the two halves of a divided neutral electrode is measured as described above. This measurement provides a guide value for the area of contact, since the resistance is proportional thereto. Furthermore, the current is measured by the neutral electrode and, taken together with the contact resistance, a theoretical power loss incurred at the electrodes is estimated. This power loss can be compared with empirically determined limit values to draw conclusions regarding the temperature at the neutral electrode. However, these approaches are highly error-prone and cannot provide reliable protection against injuring the patient. No account is taken of different tissue types therein.

SUMMARY

In the light of this prior art, and particularly U.S. application publication no. 2006/0079872 A1, it is an object herein to provide an electrosurgical device with an improved temperature measurement device. Additionally, a corresponding method for determining a temperature and/or a temperature change at a neutral electrode is disclosed. In particular, the method and the device enable reliable and efficient assessment of the temperature conditions at the neutral electrode.

This aim is achieved with an electrosurgical device comprising an HF generator for generating an HF current, which can be conducted into a biological tissue (3) via an instrument (20), and a neutral electrode (10) having a contacting agent layer (13); a temperature measurement device for determining the temperature and/or the temperature change at the neutral electrode; wherein the temperature measurement device for determining the temperature and/or the temperature change comprises an impedance measurement device, configured to detect an impedance of the contacting agent layer.

A central concept of the disclosed embodiments of the invention therefore lies in estimating the temperature of the neutral electrode or the temperature change thereof based on impedance measurements. For this purpose, the neutral electrode disclosed herein has a contacting agent layer, which has a temperature-specific impedance. The electrical resistance of the contacting agent layer changes depending on the prevailing temperature. Temperature-specific impedance within the meaning of this disclosure should be understood to mean the change in impedance depending on the temperature within a relevant temperature range. For electrosurgery, the relevant temperature range lies in the interval between 10° C. and 100° C. An interval of 20° C. to 70° C., particularly 20° C. to 60° C., could possibly suffice.

Preferably, the contacting agent layer has material properties such that the impedance decreases with increasing temperature, particularly within the relevant interval. Given local heating of the neutral electrode, the measured impedance decreases. The impedance measurement device can therefore always detect the smallest impedance and thus the section of the contacting agent layer that has the highest temperature.

The impedance measurement device can comprise a measurement current generator, which is configured to provide a measurement current at a first electrode section and at a second electrode section. Preferably, the neutral electrode is subdivided into at least one first electrode section and at least one second electrode section. Measurement of the impedance can advantageously be ensured between said two electrode sections. The measurement of a plurality of impedances between a plurality of electrode sections is also possible. In this way, improved detail resolution of the temperature conditions at the neutral electrode can be achieved. Therefore, the neutral electrode serves not only for the application of the HF current, but also for determining the impedances or impedance conditions within or at the contacting agent layer.

The measurement current generator can be configured to supply the measurement current with an alternating voltage, particularly having an alternating voltage having a frequency ≤300 kHz, particularly ≤150 kHz, and more particularly ≤100 kHz. An effective measurement of the impedance can be made with these frequencies, which are low compared to those used for the treatment with the HF current. It is possible to separate measurement currents and HF treatment currents from one another by filters and to evaluate them separately.

The electrode sections can be arranged, electrically insulated from one another, on the contacting agent layer. It is necessary to configure the electrode sections electrically insulated from one another to generate different potentials at the individual electrode sections.

The HF generator can be configured to provide an HF current with an alternating voltage at a frequency ≥300 kHz, and particularly ≥1000 kHz. These frequencies are normal in HF surgery and are suitable for carrying out advantageous coagulation and parting of tissues. These frequencies differ markedly from the frequencies used for the measurement currents. Frequency filters can be used to separate the measurement voltage from the HF voltage.

The contacting agent layer can have an electrical impedance having a high temperature dependence, particularly a (relative) impedance change of ≥1% per degree Celsius, particularly ≥2% per degree Celsius. The greater the temperature dependence of the contacting agent layer used, the more easily a temperature change can be detected from the impedance change. Preferably, the relative impedance change in the relevant temperature range is greater than 1% per degree Celsius.

The contacting agent layer can comprise or consist of hydrogel. Preferably, the contacting agent layer is made from hydrogel. On application of the HF current, hydrogel is used to reduce the contact resistance between the electrodes and the skin. The impedance of hydrogel has a strong dependence on the temperature thereof. Hydrogel is therefore very suitable for carrying out the temperature detection according to the disclosed embodiments. In this case, the hydrogel has a double function. First, the hydrogel provides for the better application of the HF current and/or for mechanical fastening of the neutral electrode to the patient. Second, the hydrogel is part of a temperature sensor.

The temperature measurement device can comprise an impedance integration device, configured to integrate impedance changes over a pre-determined time period to make thermal balance estimations. A realistic thermal balance estimation, and thus a reliable assessment of the thermal situation at the neutral electrode, can be made using long-term observation (with integration over time) of the impedance changes over all the warming up and cooling down phases in the course of an intervention.

The pre-determined time period can cover a plurality of activation and deactivation phases of the HF generator. Therefore, both the heating up during the activation phase—with the HF current applied—and the cooling down during the deactivation phase—with no HF current applied—can be taken into account for assessment of the temperature.

The electrosurgical device can comprise a recognition device for determining parameters, particularly of at least one electrode area of the neutral electrode and/or of a temperature coefficient. The impedance values measured at a neutral electrode depend on several factors. These factors include the area of the neutral electrode, particularly the area of the electrode sections, the positions thereof relative to one another, the tissue resistance, etc. It is possible to store the parameters relevant to the calculation of the temperature for specific devices and particularly for specific neutral electrodes. The recognition device can determine or read out the parameters and process them in relevant models or calculations.

The recognition device can comprise a database with a plurality of parameters and a plurality of neutral electrode types, wherein the recognition device is configured to detect the connection of a particular neutral electrode type and to read out the parameters from the database accordingly. Determination of the connected neutral electrode can therefore take place automatically (e.g., via an RFID tag situated at the neutral electrode). Numerous other methods for determining the neutral electrode types are possible. It is also possible to input the neutral electrode types manually before treatment, or to carry out the determination of the relevant parameters in a pre-determined test position.

The electrosurgical device can comprise an interruption device, configured to interrupt or limit the HF current upon exceeding a pre-determined impedance change or upon exceeding a pre-determined temperature at the neutral electrode. It is also possible for the interruption device to emit a warning signal upon exceeding a pre-determined impedance value.

The electrosurgical device can comprise a contacting agent layer with material properties such that the impedance thereof decreases with increasing temperature. This means that a material with a negative temperature coefficient can be used. It is therefore possible to detect sections of particularly low resistance caused by particularly high temperatures over the large-area neutral electrode.

In order to determine the temperature and/or the temperature change, the temperature measurement device can account for the effective value of the HF current, particularly the applied HF current. It is possible, for example, to calculate a relation between the impedance change and the effective value (e.g., $\Delta R/I_{HF}$), to determine a temperature change and/or a resistance, particularly a tissue resistance or a contact resistance between electrode and tissue. The resistance can provide information on how well a neutral electrode is attached to the tissue, among other things.

The electrosurgical device can comprise a current integration device, configured to total up a value relating to the HF current, particularly the effective value over time, particularly a pre-determined time period, and to put the total in relation to an impedance change to determine the temperature and/or the temperature change. It is easier and less error-prone if both the impedance change and the total of the applied HF current are observed over a pre-determined time interval. The individual values can be put into a relationship (e.g., $\Delta R/\Sigma I_{HF}$) to record characteristic values of the system and to determine temperature and/or temperature changes.

The aforementioned problem is also solved with a method for determining a temperature and/or a temperature change at a neutral electrode with a contacting agent layer, wherein the method comprises a) determining at least one impedance value of the contacting agent layer; and b) calculating a temperature change and/or a temperature at the neutral electrode, at least on the basis of the impedance value.

The method described herein also uses the dependency of the impedance of the contacting agent layer on the prevailing temperature. A rapid exchange of heat takes place due to the immediate proximity between the contacting agent layer and the applied part of the neutral electrode and due to the proximity between the contacting agent layer and the tissue. It can be assumed that the temperature of the tissue lying immediately beneath the neutral electrode is essentially the same as the temperature of the neutral electrode and the contacting agent layer. A realistic estimation of the temperature balance at the neutral electrode can therefore be carried out. An inadmissibly severe increase in the temperature due to the applied HF current can be recognized and prevented.

Step a) can be performed a plurality of times during a plurality of activation and deactivation phases to determine a plurality of impedance values. In this way, the temperature pattern or the individual temperature changes at the neutral electrode can be better assessed. A realistic estimation of the prevailing temperature can be carried out.

In step b), the duration of the activation and/or deactivation phase and/or an effective value of the HF current can be accounted for. Step b) can comprise the integration of a plurality of impedance values over time.

The method can comprise an impedance change during an activation phase and/or a deactivation phase. For example, it is possible, on the basis of the quotient between the cooling time and impedance change, to draw conclusions regarding the prevailing temperature. It can be assumed that, given a steeper temperature decline between the neutral electrode and the surroundings, the neutral electrode cools more rapidly. The impedance change over time can therefore represent an important parameter for determining the temperature.

Calculation of the temperature change can comprise a linear estimate, particularly using the formula:

$$\Delta T = \frac{R(T) - R(T_0)}{\alpha * R(T_0)}$$

where
$\alpha$ is a specific temperature coefficient,
$T_0$ is a starting temperature,
$R(T_0)$ is an impedance at the starting temperature $T_0$,
$R(T)$ is the measured impedance.

Although there is no linear relationship between temperature and impedance for the contacting agent used, preferably hydrogel, the change in impedance can be approximated substantially precisely in the dependence thereof on the temperature by a linear equation. Alternatively, higher order polynomial equations can be used for the approximating. The specific temperature coefficient can be determined in advance at suitable testing sites. It is also possible to determine a plurality of temperature coefficients for a higher order polynomial equation.

The method can comprise detecting a particular type of connected neutral electrode; and selecting a pre-determined temperature coefficient or of any arbitrary other parameter depending on the neutral electrode type.

Thus, parameters determined in advance can be automatically included in the method.

The method can comprise the issuing of a warning signal and/or switching off, or turning down, the HF current if the measured impedance change exceeds a pre-determined limit value. Thus, given an inadmissible temperature, a warning signal is output, and the HF current is interrupted or limited to prevent injury to the patient.

BRIEF DESCRIPTION OF THE DRAWINGS

Embodiments of the invention will now be described in more detail with reference to the drawings, wherein.

DETAILED DESCRIPTION

In the following description, the same reference signs are used for identical parts and parts acting in an identical manner.

Figure 1:
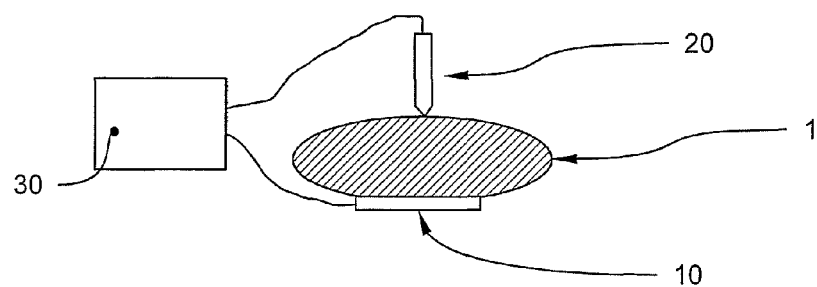
FIG. 1 shows an HF generator system with a monopolar instrument.

FIG. 1 shows an electrosurgical device comprising an HF generator system 30, a monopolar instrument 20 and a neutral electrode 10. The HF generator system 30 provides an HF current $I_{HF}$, which is applied at a torso 1 by the monopolar instrument 20 and the neutral electrode 10. FIG. 1 represents a schematic cross-section through the torso 1. The neutral electrode 10 is applied to the torso 1 over a large area thereof. The monopolar instrument 20 comprises an active electrode, which has a substantially smaller area than the neutral electrode 10. The current flows from the active electrode to the neutral electrode 10. The current density is so high in the immediate vicinity of the active electrode that targeted coagulation or parting of tissue 3 (see FIG. 3) can be performed.

Figure 2:
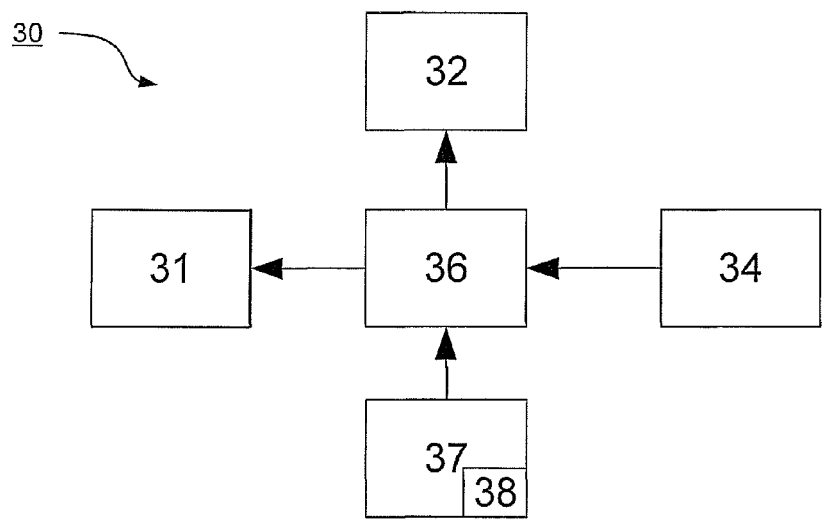
FIG. 2 shows components of the HF generator system.

FIG. 2 shows the essential components of the HF generator system 30. These components include a control device 36, display device 32, an operating device 34 and a measurement device 37. The operator of the electrosurgical device can activate or deactivate the HF current $I_{HF}$ using the operating device 34. It is also possible to set different operating modes such as for example, one mode for cutting tissue and another mode for coagulating the tissue. Depending on information from the user, the control device 36 controls the HF generator 31, which provides an HF current $I_{HF}$ according to the input. The display device 32 can be used to display set parameters such as for example, the present operating mode. The display device 32 can also display a temperature currently prevailing at the neutral electrode 10 and can output warning messages, which protect the patient against unwanted damage during the treatment. According to the disclosed embodiment, the temperature of the neutral electrode 10 is determined by the measurement device 37 using a secondary current source 38.

As soon as the neutral electrode 10 reaches a temperature that could possibly lead to burns, the HF generator 31 is switched off and the display device 32 outputs relevant warning messages.

In one exemplary embodiment of the neutral electrode 10 (see FIG. 3), the neutral electrode 10 comprises a first electrode section 11 and a second electrode section 11'. The electrode sections 11, 11' are arranged on a support material such that said sections are electrically insulated from one another.

In one embodiment of the neutral electrode 10, an electrical insulator or hydrogel 13 is situated between the individual electrode sections 11, 11'. The present exemplary embodiment uses a self-adhesive neutral electrode 10, which comprises a layer of electrically conductive hydrogel 13 that is stuck onto a tissue 3 for application of the HF current $I_{HF}$. The disclosed embodiment makes use of the fact that the hydrogel 13 has a high temperature coefficient of impedance. For example, with commercially available neutral electrodes 10 and commercially available hydrogel 13, a relative impedance change in the range of 2% to 4% per degree Celsius is measured in the temperature range from 25° C. to 40° C. This effect can be used for determining the temperature increase at the neutral electrode 10. However, various other parameters must also be accounted for. For example, the environmental conditions have a strong influence on the measured impedance R(T).

Figure 3:
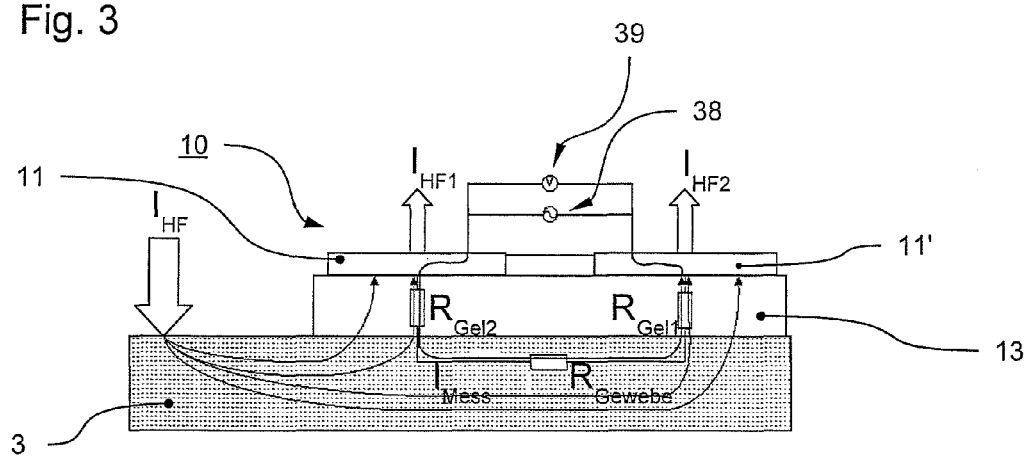
FIG. 3 shows the resistance and current conditions at a neutral electrode.

The measurement device 37 comprises the secondary current source 38 to measure the impedance R(T) dependent on the temperature T. This provides a measurement current $I_{Mess}$, which is applied to the electrode sections 11, 11'. A measurement voltage $V_{Mess}$ can be determined by a voltage measurement device 39 connected in parallel to the secondary current source 38. The measurement device 37 can thus measure the overall impedance. In a first model, it is assumed that this overall impedance, as shown in FIG. 3, is made up of a plurality of resistances. Thus, the measurement current $I_{Mess}$ passes from the first electrode section 11 through the hydrogel 13, at least partially enters the tissue 3, passes once more through the hydrogel 13 and then reaches the second electrode section 11'. The overall impedance is made up from a gel resistance $R_{Gel1}$, a tissue resistance $R_{Gewebe}$ and a second gel resistance $R_{Gel2}$.

In the first model, it can be assumed that the tissue resistance change can be ignored in the relevant temperature range (approximately 20° to 70° Celsius). The measurement device 37 can determine the gel resistance values $R_{Gel1}$, $R_{Gel2}$ from the measurement current $I_{Mess}$. The tissue resistance $R_{Gewebe}$ can be determined by further measurements or can be set to a constant value that corresponds to the approximate resistances occurring in the tissue.

In a second model, it is assumed that the gel resistance values $R_{Gel1}$, $R_{Gel2}$ are lower than the tissue resistance $R_{Gewebe}$, so that the measurement by the measurement device 37 includes only the changes in the impedance R(T) of the hydrogel 13. It is possible to select a hydrogel 13 accordingly.

In a third model, it is assumed that the resistance of the hydrogel 13 is greater than that of the tissue 3, which probably best models the use of a common hydrogel 13. This can often occur due to the small thickness of the hydrogel 13 layer. Experiments have revealed that 30% of the current flow occurs within the hydrogel layer, whereas 70% of the current flow occurs in the tissue. Situations are possible in which only approximately 10% of the current flow takes place in the hydrogel 13. As shown in FIG. 2, the impedance R(T) is made up of the gel resistance values $R_{Gel1}$, $R_{Gel2}$ and the tissue resistance $R_{Gewebe}$. Since the tissue temperature on application of the HF current $I_{HF}$ changes only very slowly compared with the temperature of the hydrogel 13—the blood circulation leads to a rapid conducting away of the generated heat energy—with this model, also, a constant or approximately constant value of $R_{Gewebe}$ can be assumed. The temperature of the tissue 3 has only a slight influence on the impedance change ΔR in the tissue. Therefore, this can be detected according to the disclosed embodiment.

Since the gel resistance values $R_{Gel1}$, $R_{Gel2}$ decline rapidly with increasing temperature T, a further advantageous effect arises. A rapid decline in the measured impedance R(T) can be detected in this region given point heating or local heating of the neutral electrode 10.

The thermal effect, which arises both in the tissue 3 and in the hydrogel 13 and at the neutral electrode 10, is attributable to the applied HF current $I_{HF}$. On use of two electrode sections 11, 11', the HF current $I_{HF}$ is divided into two HF partial currents $I_{HF1}$, $I_{HF2}$. These HF partial currents $I_{HF1}$, $I_{HF2}$ are illustrated schematically in FIG. 3.

In this exemplary embodiment, it is assumed that the relationship between the impedance R(T) of the hydrogel 13 and the temperature T thereof can be modeled sufficiently accurately with a first order temperature coefficient α. Alternatively, temperature coefficients of higher order can be included therewith.

Mathematically seen, the temperature change ΔT is found as follows:

$$\Delta T = \frac{R(T) - R(T_0)}{\alpha * R(T_0)}$$

Wherein, R(T) is the measured impedance at temperature T, $R(T_0)$ is an impedance at a starting temperature $T_0$ and α is the specific temperature coefficient. The specific temperature coefficient α can be determined, for example, within a test set-up.

Figure 4:
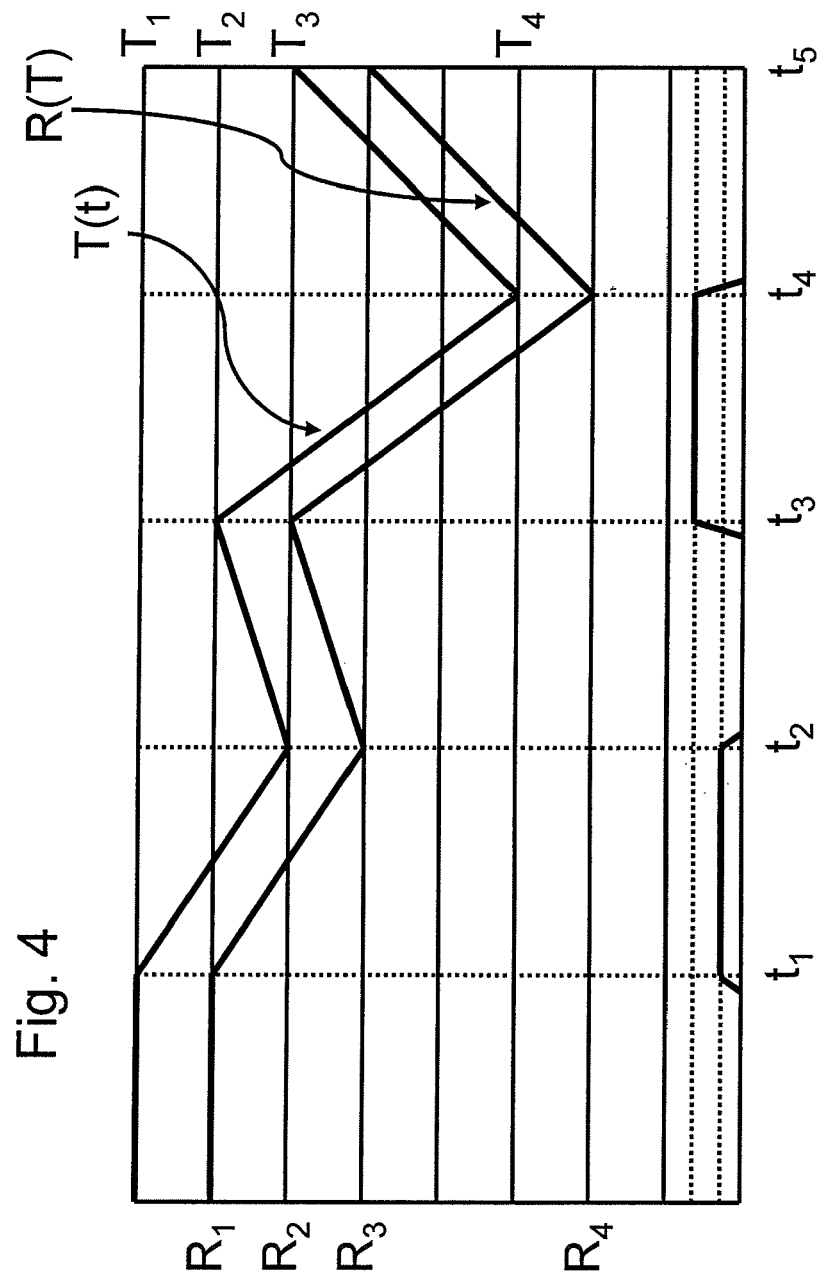
FIG. 4 shows a diagram with idealized resistance-temperature graphs.

The functioning of the measurement device 37 can be described with reference to the graph in FIG. 4.

The X-axis represents the passage of time t, in seconds. The Y-axis represents the values $R_1$, $R_2$, $R_3$, $R_4$ of a measured impedance R(T) in Ohms (lower line) and a prevailing temperature T(t) (upper line) at the neutral electrode 10 in degrees Celsius. The temperature values $T_1$, $T_2$, $T_3$, $T_4$ decline, while the impedance values $R_1$, $R_2$, $R_3$, $R_4$ increase in the Y-direction.

The graph shows, by way of example, the course of an HF treatment using a neutral electrode 10 according to the disclosed embodiments. The first temperature value $T_1$ becomes established in the hydrogel 13 immediately following application of the neutral electrode 10. The first temperature value $T_1$ essentially corresponds to the body surface temperature of approximately 32° C. The measurement device 37 can detect the first impedance value $R_1$. At time $t_1$, the HF generator 31 is activated at a low power level (schematically represented by the ramp in the graph). The activation phase continues until time $t_2$. During the activation phase, the measured impedance R(T) falls to the impedance value $R_3$. Since the starting temperature $T_1$, the starting impedance $R_1$ and the impedance value $R_2$ at time $t_2$ are known to the measurement device 37, said the measurement device 37 is able to calculate the temperature change ΔT using the above formula. Based thereon, the absolute temperature value $T_3$ can be determined.

The measured impedance R(T) rises during a deactivation phase (times $t_2$ to $t_3$). In addition, the temperature change ΔT can be determined on the basis of the impedance change ΔR, since $R_2$ is measurable and $R_3$, $T_3$ are known. Thus, the measurement device 37 can calculate the temperature $T_2$ from the current temperature change $\Delta T$. The temperature $T(t)$ of the neutral electrode rises again in a subsequent phase of activation of the HF generator 31 (times $t_3$ to $t_4$). Here again, the temperature change $\Delta T$ can be calculated.

An exemplary embodiment for the determination of the temperature $T(t)$ and the temperature change $\Delta T$ according to the present disclosure at the neutral electrode 10 has been described.

In other exemplary embodiments, other parameters can be used. For example, it is possible to take account of the temperature change $\Delta T$ during a time interval. Thus, a steep temperature fall during a relatively short deactivation phase can be used as an indicator that a relatively high temperature $T(t)$ exists at the neutral electrode 10, since there is a steep temperature decline toward the environment. Numerous other methods making use of the effect that a direct correlation exists between the impedance change $\Delta R$ of the hydrogel 13 and the temperature change $\Delta T$ thereof are possible.

The invention claimed is:

1. An electrosurgical device, comprising:
   a high frequency (HF) generator for generating an HF current, which can be conducted into a biological tissue via an instrument; and
   a neutral electrode having a contacting agent layer, wherein the contacting agent layer has material properties such that the impedance thereof decreases with increasing temperature,
   wherein the HF generator comprises a temperature measurement device for determining a temperature and/or a temperature change at the neutral electrode, the temperature measurement device comprising:
      an impedance measurement device, for determining the temperature and/or the temperature change, configured to detect an impedance of the contacting agent layer, the impedance measurement device comprises a measurement current generator, configured to provide a measurement current to a first electrode section and a second electrode section,
   wherein the temperature measurement device comprises a device configured to sum up impedance change values over a time period to make a thermal balance estimation, and
   wherein the time period comprises a plurality of activation and deactivation phases of the HF generator.

2. The electrosurgical device of claim 1, wherein the measurement current generator is configured to provide the measurement current with an alternating voltage having a frequency less than or equal to 300 kHz.

3. The electrosurgical device of claim 2, wherein the frequency is less than or equal to 150 kHz.

4. The electrosurgical device of claim 2, wherein the frequency is less than or equal to 100 kHz.

5. The electrosurgical device of claim 1, wherein the electrode sections are arranged electrically insulated from one another on the contacting agent layer.

6. The electrosurgical device of claim 1, wherein the HF generator is configured to provide an HF current with an alternating voltage at a frequency greater than or equal to 300 kHz.

7. The electrosurgical device of claim 6, wherein the HF generator is configured to provide an HF current with an alternating voltage at a frequency greater than or equal to 1000 kHz.

8. The electrosurgical device of claim 1, wherein the contacting agent layer has an electrical impedance having a temperature dependence having a relative impedance change of greater than or equal to 1% per degree Celsius.

9. The electrosurgical device of claim 8, wherein the contacting agent layer has an electrical impedance having a temperature dependence having a relative impedance change of greater than or equal to 2% per degree Celsius.

10. The electrosurgical device of claim 1, wherein the contacting agent layer comprises hydrogel.

11. The electrosurgical device of claim 1, wherein the temperature measurement device comprises an impedance integration device configured to integrate impedance changes over a pre-determined time period to make a thermal balance estimation.

12. The electrosurgical device of claim 1, further comprising a recognition device for determining parameters of at least one electrode area of the neutral electrode and/or of a temperature coefficient.

13. The electrosurgical device of claim 12, wherein the recognition device comprises a database with a plurality of parameters and a plurality of neutral electrode types and the recognition device is configured to detect the connection of a particular neutral electrode type and to read out the parameters from the database.

14. The electrosurgical device of claim 1, further comprising an interruption device configured to interrupt or limit the HF current on exceeding a pre-determined impedance change.

15. The electrosurgical device of claim 1, wherein the temperature measurement device accounts for the effective value of the HF current to determine the temperature and/or the temperature change.

16. The electrosurgical device of claim 1, further comprising:
   a current integration device, configured to total up a value relating to the HF current over time, and to put said value in relation to an impedance change to determine the temperature and/or the temperature change.

17. The electrosurgical device of claim 16, wherein the current integration device is configured to total up the effective value of the HF current over time.

18. A method for determining a temperature and/or a temperature change at a neutral electrode having a contacting agent layer, wherein the contacting agent layer has material properties such that the impedance thereof decreases with increasing temperature, the method comprising:
   determining a plurality of impedance values of the contacting agent layer, thereby detecting at least a first impedance change value during an activation phase and at least a second impedance change value during a deactivation phase; and
   calculating a temperature change and/or a temperature at the neutral electrode at least on the basis of the determined impedance change values.

19. The method of claim 18, wherein the determining step takes place at a plurality of times during a plurality of activation and deactivation phases to determine a plurality of impedance values.

20. The method of claim 19, wherein the calculating step accounts for the duration of the activation and/or deactivation phases.

21. The method of claim 19, wherein the calculating step comprises integrating a plurality of impedance values over time.

22. The method of claim 18, wherein the calculating step comprises calculating at least one quotient between impedance change and activation time or deactivation time.

23. The method of claim 22, wherein the calculating of the temperature change comprises a linear estimation using the formula:

$$\Delta T = \frac{R(T) - R(T_0)}{\alpha * R(T_0)}$$

wherein:
- $\alpha$ is a specific temperature coefficient,
- $T_0$ is a starting temperature,
- $R(T_0)$ is an impedance at the starting temperature $T_0$,
- $R(T)$ is the measured impedance.

24. The method of claim 23, further comprising:
   detecting a particular type of connected neutral electrode; and
   selecting a pre-determined temperature coefficient depending on the detected neutral electrode type.

25. The method of claim 18, further comprising outputting of a warning signal if a measured impedance change exceeds a pre-determined limit value.

26. The method of claim 18, further comprising switching off the HF current if a measured impedance change exceeds a pre-determined limit value.

27. The method of claim 18, further comprising reducing the HF current if a measured impedance change exceeds a pre-determined limit value.

28. A method for determining a temperature and/or a temperature change at a neutral electrode having a contacting agent layer, wherein the contacting agent layer has material properties such that the impedance thereof decreases with increasing temperature, the method comprising:
   detecting a particular type of connected neutral electrode;
   selecting a pre-determined temperature coefficient depending on the neutral electrode types;
   determining a plurality of impedance value of the contacting agent layer to determine impedance change values; and
   calculating a temperature change and/or a temperature at the neutral electrode at least on the basis of the impedance change values and the selected pre-determined temperature coefficient.

* * * * *